United States Patent [19]
Bui-Bertrand et al.

[11] Patent Number: 6,063,388
[45] Date of Patent: May 16, 2000

[54] PRESERVING SYSTEM AND ITS USE IN A COSMETIC OR PHARMACEUTICAL COMPOSITION

[75] Inventors: Lien Bui-Bertrand, Savigny sur Orge; Marie-Laure Carrel, Paris, both of France

[73] Assignee: L'Oreal, Paris, France

[21] Appl. No.: 08/982,424

[22] Filed: Dec. 2, 1997

[30] Foreign Application Priority Data

Dec. 24, 1996 [FR] France .................................. 96 15983

[51] Int. Cl.[7] ...................................... A61K 7/48
[52] U.S. Cl. .......................... 424/401; 514/844; 514/846; 514/532
[58] Field of Search ............................ 424/401; 514/844, 514/846, 532

[56] References Cited

U.S. PATENT DOCUMENTS

| | | | |
|---|---|---|---|
| 4,323,468 | 4/1982 | Grollier et al. | 252/174.17 |
| 4,323,694 | 4/1982 | Scala, Jr. | 560/103 |
| 4,362,747 | 12/1982 | Coursen . | |
| 4,994,265 | 2/1991 | White . | |

FOREIGN PATENT DOCUMENTS

| | | |
|---|---|---|
| 0 117 135 | 8/1984 | European Pat. Off. . |
| 2 649 718 | 1/1991 | France . |
| 94/27436 | 12/1994 | WIPO . |
| 96/36310 | 11/1996 | WIPO . |

OTHER PUBLICATIONS

Soap, Perfumery & Cosmetics, vol. 60, No. 3, 1987, pp. 47–49, P. Alexander: "Preservatives in personal care products".

*Primary Examiner*—Jyothsna Venkat
*Attorney, Agent, or Firm*—Oblon, Spivak, McClelland, Maier & Neustadt, P.C.

[57] ABSTRACT

The invention relates to a novel preserving system of at least one $C_1$–C4 alkyl para-hydroxybenzoate, sodium benzoate and N-(3-chloroallyl)hexaminium chloride. This combination finds its application most particularly in the cosmetic or pharmaceutical field, and in particular in cleansing compositions for the face and the eyes.

16 Claims, No Drawings

PRESERVING SYSTEM AND ITS USE IN A COSMETIC OR PHARMACEUTICAL COMPOSITION

BACKGROUND OF THE INVENTION

1. Field of the Invention

The invention relates to a novel preserving system comprising a combination of at least one $C_1$–$C_4$ alkyl para-hydroxybenzoate with sodium benzoate and N-(3-chloroallyl)hexaminium chloride. The invention also relates to the use of this novel system in the cosmetic and pharmaceutical fields, and in particular in compositions intended to be applied to the face and the eyes of mammals and in particular of human beings. These compositions are more especially cleansing lotions for the face and the eyes.

2. Discussion of the Background

It is common to introduce into compositions containing water, such as cosmetic or pharmaceutical compositions, in particular dermatological compositions, chemical preserving agents intended to combat the growth and proliferation of microorganisms in these compositions since such a growth of micro-organisms would rapidly make the compositions unsuitable for use. To avoid this growth, the compositions should be protected both against microorganisms capable of growing inside the compositions and against those which the user might introduce therein when handling them, in particular when the products are taken from a jar by the fingers.

The chemical preserving agents most commonly used in the above fields are, in particular, $C_1$–$C_4$ alkyl para-hydroxybenzoates, referred to hereinbelow as parabens, or formol donors. Unfortunately, these preserving agents have the drawback of causing intolerance on human skin, such as irritations and/or allergies, and more especially on sensitive skin. This is likewise the case for alcohols or polyols, such as ethanol or propylene glycol, in particular when they are present at relatively high levels. These problems of intolerance arise most particularly when the products containing these preserving agents are cleansing products and make-up-removing products for a person's face and eyes.

Moreover, it is known to use in cleansing products for the skin and the eyes, and in particular in make-up-removing lotions for the eyes, preserving agents such as benzalkonium chloride, chloroacetamide or thimerosal. Thus, document WO-A-94/27436 teaches a preserving system comprising a paraben and a quaternary ammonium compound such as benzalkonium chloride or cetylpyridinium chloride. However, the current trend and the legislation pertaining thereto are increasingly changing towards the elimination of these compounds since they are not entirely free of toxicity or of undesirable effects.

In addition, document D&CI, May 1986, 138 (5), incorporated herein by reference, at pp. 50, 52–55, and 61 describes the use of N-(3-chloroallyl)hexaminium chloride, referred to hereinbelow as Quatemium-15, as a cosmetic preserving agent and its combinations, in particular with parabens. However, the systems described in that document have the drawback of containing excessively high levels of Quatemium-15 (0.4%), which leads to eye discomfort (runny eyes, stinging, dryness, itching, redness) or allergies.

OBJECT OF THE INVENTION

It is an object of the invention to provide a novel preserving system which has an action at least as effective as the systems of the prior art but which does not have their drawbacks, and in particular which are non-irritating to the skin and the eyes.

SUMMARY OF THE INVENTION

The Applicant has found, surprisingly, that by combining sodium benzoate with parabens and Quatemium-15, a preserving system which has very good activity against microorganisms and has no problem of toxicity, while at the same time being fully tolerated by a person's skin or eyes, is obtained.

Thus, the subject of the present invention is a preserving system comprising at least one $C_1$–$C_4$ alkyl para-hydroxybenzoate and N-(3-chloroallyl)hexaminium chloride, characterized in that it also comprises sodium benzoate.

In this preserving system, each of the three preserving agents is preferably used in a lower concentration than if it was used alone or in the presence of other preserving agents; this is in keeping with better tolerance by the skin and the eyes. This system is accordingly particularly suitable for topical compositions, and in particular cosmetic and/or dermatological compositions, since it causes neither intolerance nor redness nor stinging when applied to the skin or the eyes, while at the same time having an activity against microorganisms which is at least as effective as that of the systems of the prior art which themselves cause considerable stinging.

The invention combination is effective against microorganisms such as bacteria, yeasts and molds, which are the most annoying and most common contaminants in topical compositions; it is thus particularly advantageous to use in this type of composition. Thus, a further subject of the invention is also a cosmetic and/or dermatological composition, characterized in that it contains the preserving system as defined above. The subject of the invention also includes the use of the preserving system as defined above in and/or for the preparation of a cosmetic and/or dermatological composition for limiting microbial proliferation.

The subject of the invention also includes the use of the preserving system as defined above in and/or for the preparation of a cosmetic and/or dermatological composition for removing make-up from around the eyes. Finally, the subject of the invention is also the use of the preserving system as defined above as an agent for combating microorganisms in and/or for the preparation of a cosmetic and/or dermatological composition.

DETAILED DESCRIPTION OF THE INVENTION

The $C_1$–$C_4$ alkyl para-hydroxybenzoate of the invention may be chosen, in particular, from methyl para-hydroxybenzoate, referred to hereinbelow as methylparaben, ethyl para-hydroxybenzoate, referred to hereinbelow as ethylparaben, and propyl para-hydroxybenzoate, referred to hereinbelow as propylparaben. According to a preferred mode of the invention, it is methylparaben. The preserving system according to the invention preferably comprises a weight ratio of the total amount of $C_1$–$C_4$ alkyl para-hydroxybenzoate to the sum of the amount of sodium benzoate and Quaternium-15 of 0.4 to 1.4, more preferably 0.44–1.2 including 0.6, 0.8, 1.0 and 1.1. The preferred ratio of sodium benzoate to Quaternium 15 is 3 to 20.

The topical composition containing the preserving system according to the invention preferably comprises from 0.1 to 0.15% by weight of paraben, from 0.1 to 0.2% by weight of sodium benzoate and from 0.01 to 0.03% by weight of Quaternium-15 relative to the total weight of the composition.

The compositions of the invention preferably contain a cosmetically and/or dermatologically acceptable medium, that is to say one which is compatible with the skin, mucous membranes, the hair and the scalp. They can comprise the adjuvants conventionally used in the fields considered, such as fatty substances, organic solvents, solubilizing agents, thickeners and gelling agents, softeners (allantoin), antioxidants, opacifiers, stabilizers, foaming agents, fragrances, ionic or nonionic emulsifiers, fillers, sequestering agents (disodium EDTA) and chelating agents, fragrances, screening agents, essential oils, dyestuffs, pigments, hydrophilic or lipophilic active agents, lipid vesicles encapsulating one or more active agents, or any other ingredient usually used in cosmetics or dermatology. They can also contain preserving agents other than those belonging to the system claimed. The amounts of the various constituents of the compositions according to the invention are those conventionally used in the fields considered. It goes without saying that these adjuvants must be of a nature and used in an amount such that they do not perturb the preserving system according to the invention.

The compositions according to the invention can be in any cosmetic, dermatologic or pharmaceutical form which is appropriate for topical application and preferably includes a vehicle, in particular in the form of aqueous, aqueous-alcoholic or oily solutions, aqueous, aqueous-alcoholic or oily gels, pasty or solid anhydrous products, emulsions obtained by dispersing a fatty phase in an aqueous phase (O/W), or conversely (W/O), suspensions, microemulsions, microcapsules, microparticles, or alternatively vesicle dispersions of ionic type (liposomes) and/or nonionic type. In the vesicle dispersions, the vesicles do not necessarily contain an active agent, and serve to disperse and/or stabilize an oily phase in an aqueous phase.

The compositions of the invention can thus have the appearance of a cream, a lotion, a milk, a serum, etc. The compositions according to the invention can also be used in the form of foams or alternatively in the form of aerosol compositions also containing a propellant under pressure.

When the composition of the invention is an emulsion, the proportion of the fatty phase preferably ranges from 5 to 80% by weight, more preferably from 5 to 50% by weight, relative to the total weight of the composition. The oils, the emulsifiers and the co-emulsifiers used in the composition in emulsion form are chosen from those conventionally used in the cosmetic or dermatological field. The emulsifier and optionally the co-emulsifier are present in the composition in a proportion ranging from 0.3 to 30% by weight, and preferably from 0.5 to 20% by weight, relative to the total weight of the composition.

Oils which can be used in the invention include mineral oils (isoparaffin), oils of plant origin (apricot kernel oil, sweet almond oil), oils of animal origin, synthetic oils (octyl palmitate, isopropyl palmitate), silicone oils (cyclopenta-dimethylsiloxane) and fluoro oils. Fatty alcohols, fatty acids and waxes can also be used as fatty substances.

Invention emulsifiers include, for example, of the mixture of glyceryl stearate and PEG-100 stearate, sold under the name Arlacel 165 by the company ICI, the mixture of coconut acid ethanolamides (CTFA name: Cocamide DEA), disodium cocoamphodiacetate and oxyethylenated, oxypropylenated block polymers such as Poloxamer 184 (CTFA name).

Surfactants such as the mixture sodium laureth sulphate/magnesium laureth sulphate/sodium laureth-8 sulphate/magnesium laureth-8 sulphate, sold under the name "Texapon ASV" by the company Henkel, can be added thereto.

Useful hydrophilic gelling agents include, in particular, carboxyvinyl polymers (carbomer), acrylic copolymers such as acrylate/alkyl acrylate copolymers (Pemulen), polyacrylamides, polysaccharides, natural gums (xanthan gum) and clays, and, as lipophilic gelling agents, mention may be made of modified clays such as bentones, metal salts of fatty acids, hydrophobic silica and polyethylenes.

The compositions according to the invention are prepared according to techniques that are well known to those skilled in the art. These compositions preferably constitute cleansing products and make-up-removing products for the skin and the eyes, and in particular cleansing lotions and make-up-removing lotions. Thus, the subject of the present invention is also a cleansing and/or make-up-removing lotion for the skin and/or the eyes, characterized in that it contains the preserving system as defined above.

The lotion according to the invention can in particular comprise, as adjuvants, at least one nonionic and/or anionic surfactant. Moreover, it can also comprise at least one glycol such as propylene glycol, butylene glycol and hexylene glycol.

Other characteristics and advantages of the invention may become apparent in the examples which follow, which are given purely by way of illustration and without any limitation at all implied.

EXAMPLES

Hereinbelow, the percentages are given by weight except where otherwise mentioned.

The following test demonstrates the activity of the combination according to the invention on micro-organisms.

The steps for carrying out this test are as follows:

1) Culturing of the microorganism of the strains used:
   *Escherichia coli* (bacterium)
   *Pseudomonas aeruginosa* (bacterium)
   *Enterococcusfaecalis* (bacterium)
   *Candida albicans* (yeast)
   *Aspergillus niger* (mold)
   The strains are prepared in tryptone-salt culture medium.

2) Preparation of the inoculum: The inoculum consists of a 24-hour-old culture of the test microorganism on an appropriate agar nutrient medium diluted so as to obtain a suspension containing $10^5$ to $10^6$ microorganisms/ml. Counting of 5 inocula is carried out.

3) Preparation of the sample: 20 g of the test product are placed in 5 glass containers known as pill bottles.

4) Inoculation: 0.2 ml of inoculum of each strain is introduced into each pill bottle and is homogenized. The pill bottles are then incubated at 22° C. for 7 days.

5) Removal and counting:

After incubation for 7 days, 1 g of product is taken from each of the pill bottles. Tenfold dilutions are carried out in a diluent containing preserving agent-inhibitors which will stop the action of the preserving agents. These dilutions are plated out onto the surface of agar Petri dishes and then incubated at 35° C. for 72 hours for the bacteria and yeasts and for 5 days for the molds. The colonies which form are then counted, taking the dilutions into account.

Example 1
Preserving System
The test system has the following composition:

| | |
|---|---|
| Methylparaben | 0.15% |
| Quaternium-15 | 0.015% |
| Sodium benzoate | 0.13% |

The results obtained are collated in Table 1.

TABLE 1

| Microorganisms | Inoculum micro-organisms/gram | Microorganisms surviving at 7 days |
|---|---|---|
| *Escherichia coli* | $3.4 \times 10^6$ | <200* |
| *Pseudomonas aeruginosa* | $5.3 \times 10^6$ | <200* |
| *Enterococcus faecalis* | $3.4 \times 10^6$ | $4 \times 10^4$ |
| *Candida albicans* | $3.5 \times 10^6$ | <200* |
| *Aspergillus niger* | $1.2 \times 10^6$ | $1.4 \times 10^3$ |

*Sensitivity threshold of the method

The results show a decrease of at least 2 log units for the microorganisms, which represents a satisfactory amount.

Example 2
Preserving System
The test system has the following composition:

| | |
|---|---|
| Methylparaben | 0.1% |
| Quaternium-15 | 0.018% |
| Sodium benzoate | 0.1% |

The results obtained are collated in Table 2.

TABLE 2

| Microorganisms | Inoculum microorganisms/gram | Microorganisms surviving at 7 days |
|---|---|---|
| *Escherichia coli* | $2.5 \times 10^6$ | <200* |
| *Pseudomonas aeruginosa* | $3.1 \times 10^6$ | <200* |
| *Enterococcus faecalis* | $2.1 \times 10^6$ | <200* |
| *Candida albicans* | $3.1 \times 10^6$ | <200* |
| *Aspergillus niger* | $4 \times 10^6$ | $5.8 \times 10^3$ |

*Sensitivity threshold of the method

The table shows that the system according to the invention gives very good results: microorganisms are no longer detectable for the bacteria and yeast, and the amount of mold microorganisms is greatly reduced.

Example 3
Make-up-removing Milk

| | |
|---|---|
| Isopropyl palmitate | 5% |
| Apricot kernel oil | 0.25% |
| Sweet almond oil | 0.25% |
| Methylparaben | 0.15% |
| Quaternium-15 | 0.025% |
| Sodium benzoate | 0.1% |
| Disodium EDTA | 0.05% |
| Sodium hydroxide | 0.1% |
| Carbomer | 0.25% |
| Xanthan gum | 0.1% |
| Glycerol | 3% |
| Cocamide DEA | 0.5% |
| Arlacel 165 | 1.7% |
| Demineralized water | qs 100% |

This milk allows make-up to be removed from the face without irritation.

Example 4
Make-up-removing Water

| | |
|---|---|
| Methylparaben | 0.1% |
| Quaternium-15 | 0.025% |
| Sodium benzoate | 0.2% |
| Fragrance | 0.04% |
| Sodium hydroxide | 0.025% |
| Disodium EDTA | 0.05% |
| Poloxamer 184 | 2% |
| Demineralized water | qs 100% |

This make-up-removing water can be used to remove make-up from the face and around the eyes in total safety, that is to say without causing any eye discomfort.

Example 5
Make-up-removing Lotion

| | |
|---|---|
| Allantoin | 0.05% |
| Methylparaben | 0.15% |
| Quaternium-15 | 0.018% |
| Sodium benzoate | 0.1% |
| Fragrance | 0.01% |
| Sodium chloride | 0.09% |
| Disodium EDTA | 0.05% |
| Propylene glycol | 1% |
| Disodium cocoamphodiacetate | 2% |
| Texapon ASV | 0.5% |
| Demineralized water | qs 100% |

This make-up-removing lotion allows make-up to be removed from around the eyes in total comfort, that is to say without causing any eye discomfort.

Example 6
Two-in-one Make-up-removing Product

| | |
|---|---|
| Octyl palmitate | 15% |
| Methylparaben | 0.15% |
| Quaternium-15 | 0.025% |
| Sodium benzoate | 0.1% |
| Disodium EDTA | 0.1% |
| Triethanolamine | 0.82% |
| Pemulen | 0.15% |
| Carbomer | 0.42% |
| Glycerol | 5% |
| Texapon ASV | 0.9% |
| Disodium cocoamphodiacetate | 0.5% |
| Demineralized water | qs 100% |

This make-up-removing product can be used both for the face and for around the eyes and is very comfortable to use.

French patent application 96-15983 is incorporated herein by reference.

What is claimed as new and is desired to be secured by Letters: Patent of the United States is:

1. A composition comprising 0.1 to 15% by weight of the at least one $C_1$–$C_4$ alkyl para-hydroxy benzoate, 0.01 to 0.03% by weight of N-(3-chloroallyl)hexaminium chloride, and 0.1 to 0.2% by weight of sodium benzoate relative to the total weight of the composition.

2. The composition according to claim 1, wherein the $C_1$–$C_4$ alkyl para-hydroxybenzoate is selected from the group consisting of methyl para-hydroxybenzoate, ethyl para-hydroxybenzoate and propyl para-hydroxybenzoate.

3. The composition according to claim 1, where in $C_1$–$C_4$ alkyl para-hydroxy benzoate is methyl para-hydroxybenzoate.

4. The composition according to claim 1, wherein the weight ratio of the amount of $C_1$–$C_4$ alkyl para-hydroxybenzoate to the sum of the amount of sodium benzoate and N-(3-chloroallyl)hexaminium chloride is from 0.4 to 1.4.

5. The composition according to claim 1, further comprising a vehicle.

6. The composition according to claim 1, in the form of a cleansing, make-up-removing or both cleansing and make-up-removing composition.

7. The composition according claim 6, in the form of a composition for removing make-up from around the eyes.

8. The composition according to claim 1, in the form of an aqueous or aqueous-alcoholic solution, an emulsion, a microemulsion, an aqueous or anhydrous gel, or a vesicle dispersion.

9. The composition according to claim 1, in the form of a lotion.

10. The composition according to claim 1, further comprising at least one adjuvant selected from the group consisting of fatty substances, organic solvents, solubilizing agents, gelling agents, foaming agents, emulsifiers, fillers, pigments, hydrophilic or lipophilic active agents and lipid vesicles.

11. The composition according to claim 1, further comprising nonionic, anionic or both nonionic and anionic surfactant.

12. The composition according to claim 11, further comprising at least one glycol.

13. The composition according to claim 9, further comprising at least one glycol.

14. A method for preparing a stable composition, comprising adding to said composition 0.1 or 15% by weight of the at least one $C_1$–$C_4$ alkyl para-hydroxy benzoate, 0.01 to 0.03% by weight of N-(3-chloroallyl)hexaminium chloride, and 0.1 to 0.2% by weight of sodium benzoate relative to the total weight of the composition.

15. A method for cleaning the skin, comprising applying the composition of claim 1 to the skin and removing said composition from the skin.

16. A method for treating the skin, comprising applying the composition of claim 1 to the skin and removing said composition from the skin.

* * * * *